United States Patent
Tojo et al.

(10) Patent No.: US 10,502,693 B2
(45) Date of Patent: Dec. 10, 2019

(54) INSERTION/REMOVAL APPARATUS, INSERTION SECTION DIRECT MANIPULATION ESTIMATION METHOD AND STORAGE MEDIUM WHICH NON-TRANSITORY STORES INSERTION SECTION DIRECT MANIPULATION ESTIMATION PROGRAM

(71) Applicant: OLYMPUS CORPORATION, Tokyo (JP)

(72) Inventors: Ryo Tojo, Hachioji (JP); Takeshi Ito, Hino (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 189 days.

(21) Appl. No.: 15/726,453

(22) Filed: Oct. 6, 2017

(65) Prior Publication Data

US 2018/0031493 A1    Feb. 1, 2018

Related U.S. Application Data

(63) Continuation of application No. PCT/JP2015/060842, filed on Apr. 7, 2015.

(51) Int. Cl.
*G01N 21/954* (2006.01)
*G01B 11/24* (2006.01)
(Continued)

(52) U.S. Cl.
CPC .......... *G01N 21/954* (2013.01); *G01B 11/24* (2013.01); *G01D 5/35341* (2013.01);
(Continued)

(58) Field of Classification Search
None
See application file for complete search history.

(56) References Cited

U.S. PATENT DOCUMENTS

2009/0030306 A1    1/2009  Miyoshi et al.

FOREIGN PATENT DOCUMENTS

| CN | 101155540 A | 4/2008 |
|---|---|---|
| JP | 2007-044412 A | 2/2007 |

(Continued)

OTHER PUBLICATIONS

English translation of International Preliminary Report on Patentability dated Oct. 19, 2017 together with the Written Opinion received in related International Application No. PCT/JP2015/060842.

(Continued)

*Primary Examiner* — James M Anderson, II
(74) *Attorney, Agent, or Firm* — Scully, Scott, Murphy & Presser, P.C.

(57) ABSTRACT

A insertion/removal apparatus comprises an insertion section with flexibility which is inserted into a target object to perform a desired operation, a shape sensor, an insertion section shape calculator, and a direct manipulation information estimation circuit. The shape sensor detects bending of the insertion section and outputs a detection signal. The insertion section shape calculator which calculates insertion section shape information indicating a shape of the insertion section, based on the detection signal output from the shape sensor. The direct manipulation information estimation circuit which estimates direct manipulation information including at least one of an insertion/removal amount and a rotation amount of the insertion section inserted into and removed from the target object, based on the insertion section shape information.

13 Claims, 11 Drawing Sheets

(51) Int. Cl.
*G01D 5/353* (2006.01)
*G02B 23/24* (2006.01)
*H04N 5/225* (2006.01)
*A61B 1/00* (2006.01)
*A61B 1/005* (2006.01)
*A61B 1/01* (2006.01)

(52) U.S. Cl.
CPC ..... *G01D 5/35345* (2013.01); *G02B 23/2446* (2013.01); *H04N 5/2256* (2013.01); *A61B 1/0002* (2013.01); *A61B 1/00009* (2013.01); *A61B 1/00045* (2013.01); *A61B 1/00055* (2013.01); *A61B 1/0057* (2013.01); *A61B 1/00071* (2013.01); *A61B 1/01* (2013.01); *G01N 2021/9542* (2013.01); *H04N 2005/2255* (2013.01)

(56) References Cited

FOREIGN PATENT DOCUMENTS

| | | |
|---|---|---|
| JP | 2013-039312 A | 2/2013 |
| JP | 2014-117446 A | 6/2014 |
| JP | 2015-024033 A | 2/2015 |
| WO | WO 2006/114935 A1 | 11/2006 |
| WO | WO 2014/065336 A1 | 5/2014 |

OTHER PUBLICATIONS

Japanese Office Action dated Jul. 24, 2018 in Japanese Patent Application No. 2017-510832.
Chinese Office Action dated Sep. 25, 2018 in Chinese Patent Application No. 201580078645.X.
International Search Report dated Jul. 7, 2015 issued in PCT/JP2015/060842.

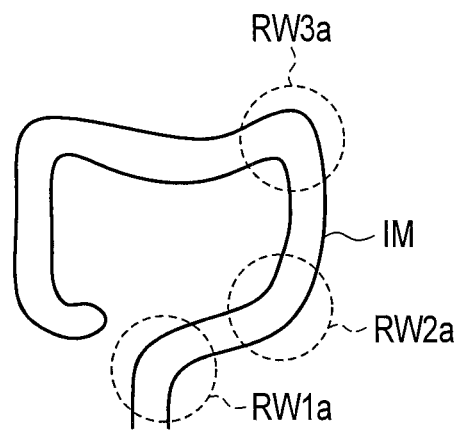
F I G. 12A
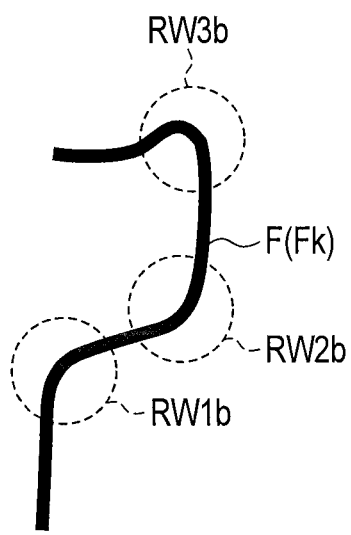
F I G. 12B

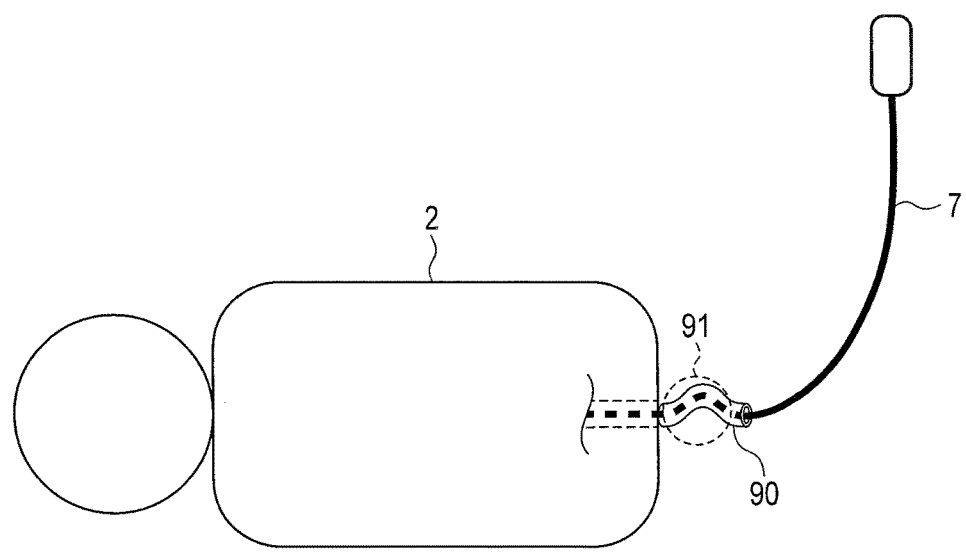
F I G. 13
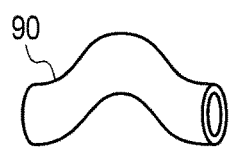
F I G. 14A
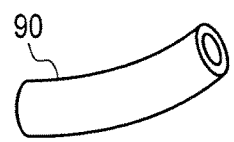
F I G. 14B
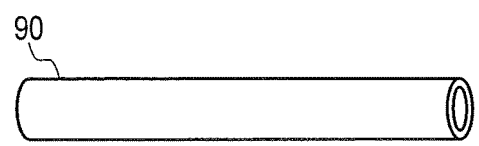
F I G. 14C

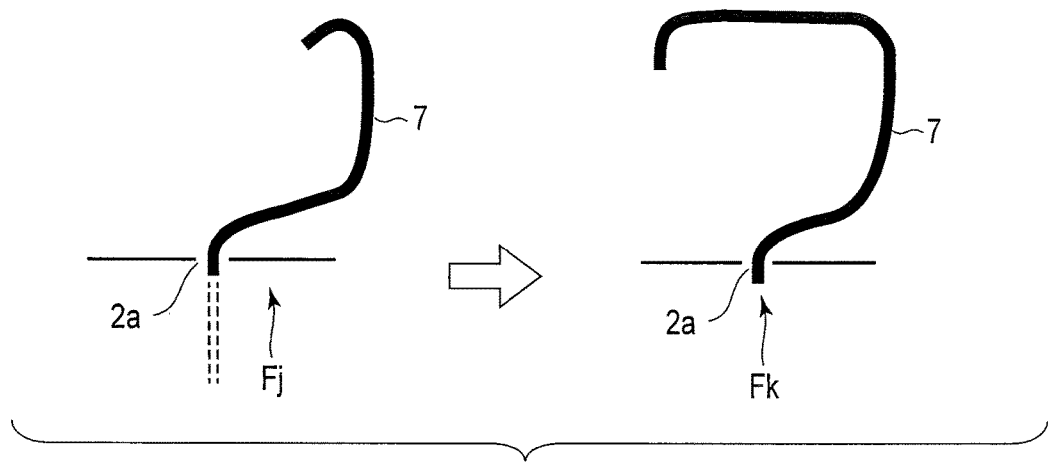
F I G. 15
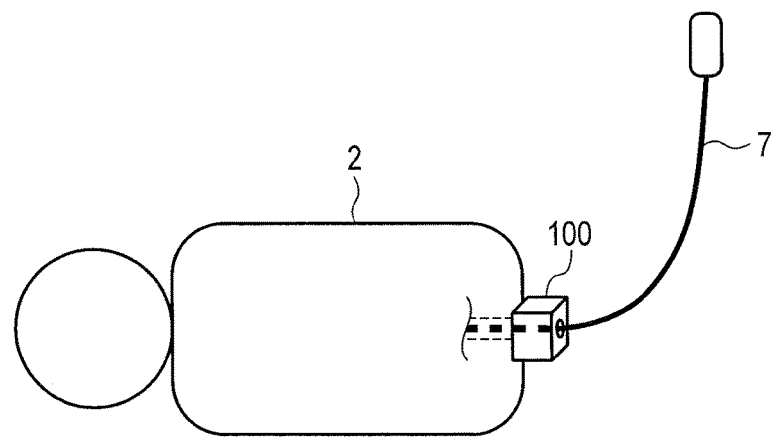
F I G. 16

INSERTION/REMOVAL APPARATUS, INSERTION SECTION DIRECT MANIPULATION ESTIMATION METHOD AND STORAGE MEDIUM WHICH NON-TRANSITORY STORES INSERTION SECTION DIRECT MANIPULATION ESTIMATION PROGRAM

CROSS-REFERENCE TO RELATED APPLICATION

This application is a Continuation Application of PCT Application No. PCT/JP2015/060842, filed Apr. 7, 2015, the entire contents of which are incorporated herein by reference.

BACKGROUND OF THE INVENTION

1. Field of the Invention

The present invention relates to an insertion/removal apparatus for estimating a manipulation amount such as an insertion/removal amount and a rotation amount of an insertion section that is inserted into an observation target object, and a method for estimating a direct manipulation of the insertion section, and a storage medium which non-transitory stores a program for estimating a direct manipulation of the insertion section.

2. Description of the Related Art

There is an apparatus for performing an operation inside an observation target object by inserting an insertion section into the observation target object through a thin tube hole. For example, an endoscope is intended to observe the inner surface of an observation target object by inserting an insertion section into the observation target object. An apparatus such as the endoscope makes it impossible to observe, e.g. the shape of an insertion section in a tube directly from the outside. Therefore, an operator of the apparatus needs to observe the inner surface of an observation target object while imagining a state of the insertion section in the tube.

In the endoscope, however, the state of the insertion section, such as the position and shape thereof, in the observation target object cannot be seen from outside the observation target object. Thus, an operator needs to make an observation while imagining where in the tube hole the insertion section is located and what is observed at the present time regarding the state of the insertion section inserted into the tube hole. In short, an operator needs to manipulate the insertion section by intuition while imagining the state of the insertion section inside the observation target object.

As is seen from the above, when the shape of a tube hole is complex or when an observation target object is soft and deformed like a living body, the insertion into the observation target object itself could be difficult. When a tube hole differs in position or shape from what an operator imagined, it is likely to exert an influence on the observation target object as a worst case. Therefore, the operator needs to improve his or her operation skill, such as long hours of training for operation and gaining of intuition and experience during the actual operation. In other words, if an operator is not a highly-trained technician or expert, he or she could not insert the insertion section into the observation target object or perform an operation in the observation target object.

Under the circumstances described above, a technique of notifying an operator of the state of an insertion section in a tube hole is devised. For example, Jpn. Pat. Appln. KOKAI Publication No. 2007-044412 discloses an endoscope insertion shape probe for detecting a shape of an insertion section of an endoscope and displaying it. The endoscope insertion shape detection probe is inserted into a forceps channel provided in an endoscope apparatus to detect the shape of the insertion section of the endoscope. The endoscope insertion shape detection probe irradiates a mirror with light supplied from a light supply fiber and transmits the light reflected by the mirror through a plurality of curvature detection optical fibers. Each of the curvature detection optical fibers is provided with one optical loss section that varies in optical loss according to a corresponding curvature. Accordingly, the light guided by each of the curvature detection optical fibers reaches a module via the optical loss section. It is thus possible to detect the curvature of a curvature detection optical fiber in a position where the optical loss section is provided, by detecting a change of intensity of the light guided to the module.

Jpn. Pat. Appln. KOKAI Publication No. 2007-044412 also discloses using a plurality of curvature detection fibers whose optical loss sections are provided in different positions to detect the curvatures of the curvature detection fibers at the different positions of the optical loss sections, respectively. It is thus possible to detect the shape of an endoscope insertion section in accordance with the bending angle at a point where each optical loss section is provided and the distance between adjacent points.

BRIEF SUMMARY OF THE INVENTION

According to a first aspect of the present invention, there is provided an insertion/removal apparatus comprising: an insertion section with flexibility which is inserted into a target object to perform a desired operation; a shape sensor which detects bending of the insertion section and outputs a detection signal; an insertion section shape calculator which calculates insertion section shape information indicating a shape of the insertion section, based on the detection signal output from the shape sensor; and a direct manipulation information estimation circuit which estimates direct manipulation information including at least one of an insertion/removal amount and a rotation amount of the insertion section inserted into and removed from the target object, based on the insertion section shape information, wherein the shape sensor detects bindings of the insertion section with different detection timings, wherein the direct manipulation information estimation circuit includes a shape information storage which stores a plurality of items of insertion section shape information indicating shapes of the insertion section of the different detection timings, and compares the plurality of items of insertion section shape information and estimates the direct manipulation information, and wherein the direct manipulation information estimation circuit extracts regions whose shapes are similar on the insertion section as insertion section similar shape regions from a result of comparison of the plurality of items of insertion section shape information, and estimates the direct manipulation information based on variations in position of the insertion section similar shape regions on the insertion section.

According to a second aspect of the present invention, there is provided an insertion/removal apparatus comprising: an insertion section with flexibility which is inserted into a target object to perform a desired operation; a shape sensor which detects bending of the insertion section and outputs a detection signal; an insertion section shape calculator which calculates insertion section shape information indicating a shape of the insertion section, based on the detection signal output from the shape sensor; and a direct manipulation information estimation circuit which estimates direct manipulation information including at least one of an insertion/removal amount and a rotation amount of the insertion section inserted into and removed from the target object, based on the insertion section shape information, wherein the shape sensor detects bindings of the insertion section with different detection timings, wherein the direct manipulation information estimation circuit includes a shape information storage which stores a plurality of items of insertion section shape information indicating shapes of the insertion section of the different detection timings, and compares the plurality of items of insertion section shape information and estimates the direct manipulation information, and wherein the direct manipulation information estimation circuit compares the plurality of items of insertion section shape information acquired with the different detection timings, extracts a first inter-top distance same region in which intervals between tops of a plurality of bending portions of the insertion section are substantially equal to each other, and estimates the direct manipulation information based on variations in position of the first inter-top distance same region on the insert section.

According to a third aspect of the present invention, there is provided an insertion/removal apparatus comprising: an insertion section with flexibility which is inserted into a target object to perform a desired operation; a shape sensor which detects bending of the insertion section and outputs a detection signal; an insertion section shape calculator which calculates insertion section shape information indicating a shape of the insertion section, based on the detection signal output from the shape sensor; and a direct manipulation information estimation circuit which estimates direct manipulation information including at least one of an insertion/removal amount and a rotation amount of the insertion section inserted into and removed from the target object, based on the insertion section shape information, wherein the direct manipulation information estimation circuit includes a storage section which stores target object inner shape information that is an inner shape of the target object, and estimates the direct manipulation information based on the insertion section shape information and the target object inner shape information.

According to a fourth aspect of the present invention, there is provided an insertion section direct manipulation estimation method comprising: detecting bending of an insertion section with flexibility by a shape sensor when the insertion section is inserted into a target object to perform a desired operation; calculating insertion section shape information indicating a shape of the insertion section, based on the detection signal output from the shape sensor; and estimating direct manipulation information including at least one of an insertion/removal amount and a rotation amount of the insertion section inserted into and removed from the target object, based on the insertion section shape information, wherein the shape sensor detects bindings of the insertion section with different detection timings, and wherein the estimating direct manipulation information includes: comparing a plurality of items of insertion section shape information which is stored in a shape information storage and which indicates shapes of the insertion section of the different detection timings; extracting regions whose shapes are similar on the insertion section as insertion section similar shape regions from a result of comparison of the plurality of items of insertion section shape information; and estimating the direct manipulation information based on variations in position of the insertion section similar shape regions on the insertion section.

According to a fifth aspect of the present invention, there is provided a storage medium, which non-transitory stores a computer-readable insertion section direct manipulation estimation program, causing a computer to achieve: an input function of inputting a detection signal output from a shape sensor to detect bending of an insertion section with flexibility inserted into a target object; an insertion section shape acquisition function of calculating insertion section shape information indicating a shape of the insertion section, based on the detection signal input by the input function; and a direct manipulation information estimation function of estimating direct manipulation information including at least one of an insertion/removal amount and a rotation amount of the insertion section inserted into and removed from the target object, based on the insertion section shape information, wherein the shape sensor detects bindings of the insertion section with different detection timings, and wherein the direct manipulation information estimation function includes: a comparing function of computing a plurality of items of insertion section shape information which is stored in a shape information storage and which indicates shapes of the insertion section of the different detection timings; an extracting function of extracting regions whose shapes are similar on the insertion section as insertion section similar shape regions from a result of comparison of the plurality of items of insertion section shape information; and an estimating function of estimating the direct manipulation information based on variations in position of the insertion section similar shape regions on the insertion section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 12A is an illustration of a second inter-top distance same region in a target object inner shape extracted by the direct manipulation information estimation circuit in the apparatus.

FIG. 12B is an illustration of a second inter-top distance same region in an insertion section shape extracted by the direct manipulation information estimation circuit in the apparatus.

FIG. 13 is an illustration of a fixed-shape generation attachment.

FIG. 14A is an illustration of an attachment with a bending portion.

FIG. 14B is an illustration of an attachment that is bent with a preset small curvature.

FIG. 14C is an illustration of an attachment shaped like a linear cylinder with a length that the inside of an observation target object cannot have.

FIG. 15 is an illustration of an example of the first to third characteristic portions in the j-th and k-th insertion section shapes Fj and Fk upon detection.

FIG. 16 is an illustration of an insertion/removal rotation amount sensor which directly senses at least one of the insertion/removal amount and the rotation amount of the insertion section as direct manipulation information.

DETAILED DESCRIPTION OF THE INVENTION

[First Embodiment]

A first embodiment of the present invention will be described below with reference to the drawings.

Figure 1:
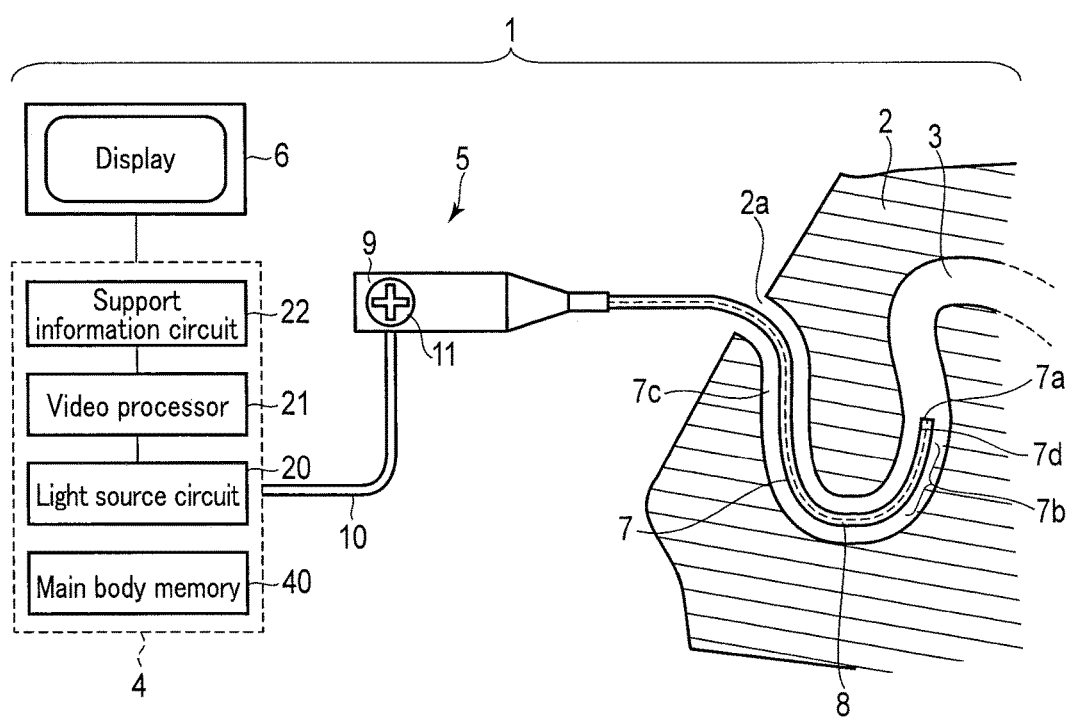
FIG. 1 is a block diagram showing a first embodiment of an endoscope system to which an insertion/removal apparatus of the present invention is applied.

FIG. 1 is a block diagram showing an endoscope system 1 to which an insertion/removal apparatus is applied. This system 1 is used mainly to insert an endoscope insertion section (referred to as an insertion section hereinafter) 7 into an internal space (hollow) 3 of an observation target object 2 through an operator's operation to observe the inner surface of the internal space 3 of the observation target object 2.

The system 1 includes an endoscope main body 4, an endoscope unit 5 and a display 6 as configuration elements. The endoscope unit 5 includes the insertion section 7. The insertion section 7 is loaded with a shape sensor 8.

The configuration elements of the system 1 will be described.

[Endoscope Unit]

The endoscope unit 5 includes the insertion section 7, a control section 9 and a cable 10. The endoscope unit 5 is grasped and manipulated by an operator. By this manipulation, the insertion section 7 of the endoscope unit 5 is moved to an insertable position from an insertion opening 2a as an entrance portion of the observation target object 2 and inserted into the internal space 3 of the observation target object 2.

The cable 10 is intended to connect the endoscope unit 5 and the endoscope main body 4 and is detachable from the endoscope main body 4. The system 1 may include one or more cables 10 and the cable(s) is connected between the endoscope unit 5 and the endoscope main body 4.

The insertion section 7 will be described specifically. The insertion section 7 is formed of a distal-end portion 7a and the other portion. The distal-end portion 7a includes a region formed hard (a hard portion). The other region of the distal-end portion 7a is formed flexibly. The hard portion of the distal-end portion 7a is formed in a preset region (a small region). In part of the flexible region of the insertion section 7, which is near the distal-end portion 7a, an active bending portion 7b is formed such that it can be bent actively. The active bending portion 7b is bent actively in vertical or horizontal directions if an operator manipulates a control handle 11 provided in the control section 9. In the other region of the insertion section 7, a passive bending portion 7c is formed such that it can be bent passively. The passive bending portion 7c is bent passively after the shape of the observation target object 2. The passive bending portion 7c is bent passively depending on the way of operator's grasping, the relationship in position between the insertion opening 2a for the observation target object 2 and the control section 9, or the like.

The control section 9 includes the control handle 11. The operator manipulates the control handle 11 to bend the active bending portion 7b of the insertion section 7 in a vertical or horizontal direction. For example, the operator grasps the control section 9 with his or her one hand to manipulate the control handle 11 and thus bend the active bending portion 7b of the insertion section 7 in a vertical or horizontal direction. Upon receiving the operator's manipulation of the control handle 11, the control section 9 allows the bending amount of the active bending portion 7b to vary in the insertion section 7.

A plurality of paired manipulation wires are provided between the insertion section 7 and the control handle 11. These manipulation wires are used for bending in a vertical direction and bending in a horizontal direction. These manipulation wires are formed like a loop, for example. When the control handle 11 turns, the manipulation wires move between the insertion section 7 and the control handle 11 to transmit the turn of the control handle 11 to the insertion section 7. Thus, the active bending portion 7*b* of the insertion section 7 is bent in the vertical or horizontal direction in accordance with the control amount of the control handle 11.

Figure 2:
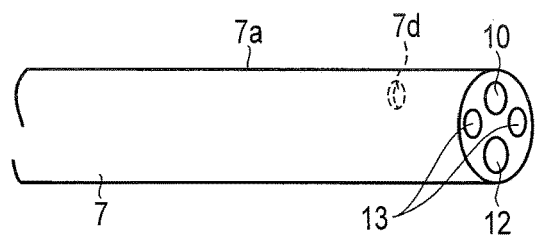
FIG. 2 is a configuration diagram of a distal-end portion of an insertion section.

FIG. 2 is a configuration diagram of the distal-end portion 7*a* of the insertion section 7 in the system 1. The distal-end portion 7*a* of the insertion section 7 is provided with various members corresponding to the use of the endoscope unit 5, including an image sensor 7*d*, an objective lens 10, an instrument channel 12 and an illumination section 13. The objective lens 10 is optically connected to the image sensor 7*d*. The instrument channel 12 is an opening into which, e.g. forceps are inserted to perform various types of operation and treatment in the internal space 3 of the observation target object 2. The illumination section 13 emits light from a light source section 20 of the endoscope main body 4 toward the internal space 3 of the observation target object 2.

In the system, 1, when the internal space 3 of the observation target object 2 is irradiated with the light emitted from the illumination section 13 of the insertion section 7, the light is reflected by the internal space 3 of the observation target object 2 and enters the objective lens 10. The image sensor 7*d* is provided at the distal-end portion 7*a* of the insertion section 7. The image sensor 7*d* photoelectrically convert light incident upon the objective lens 10 and then output an imaging signal. This imaging signal is sent to a video processor 21 through the cable 10. The video processor 21 processes the imaging signal output from the image sensor 7*d* to acquire an observation image of the inner surface of the observation target object 21. This observation image is displayed on the display 6.

The display 6 can display the internal space 3 of the observation target object 2 to be observed by the system 1, information about the observation target object 2 which is previously stored in the main body memory 40 of the endoscope main body 4, information about an observation operation to observe the observation target object 2, and the direct manipulation information DM output from a support information circuit 22 (described later). The display 6 includes a monitor display of liquid crystal, a CRT, an LED, plasma or the like. For convenience's sake, FIG. 1 shows one display 6, but the number of displays is not limited to one. Two or more displays can be arranged side by side or a plurality of displays can be arranged in different locations.

The display 6 is not limited only to displaying images and character information on the monitor display. The display 6 here includes an output for aural recognition using voice, alarm sound or the like and an output for tactile recognition using vibration or the like. The display 6 is a general term of an output device using various information transmission techniques of informing an operator of information.

The insertion section 7 includes the active bending portion 7*b* bent by the manipulation of the control handle 11 and the passive bending portion 7*c* bent passively. The passive bending portion 7*c* is pushed against the wall surface of the internal space 3 of the observation target object 2 and thus bent after the shape of the wall surface of the internal space 3. If, therefore, the insertion section 7 is inserted into the internal space 3 of the observation target object 2, it moves in the internal space 3 of the observation target object 2 while being pushed against the wall surface of the internal space 3. The internal space 3 of the observation target object 2 may include introduction channels of, e.g. different shapes depending on, e.g. the type of the observation target object 2. The insertion section 7 therefore has a configuration capable of moving in the internal space 3 of the observation target object 2.

Figure 3A:
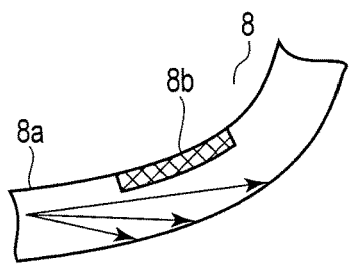
FIG. 3A is an illustration of a light transmission amount used when an optical fiber sensor is bent toward a shape detector.
Figure 3B:
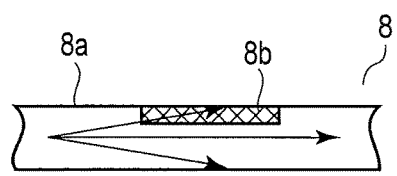
FIG. 3B is an illustration of a light transmission amount used when the optical fiber sensor is not bent.
Figure 3C:
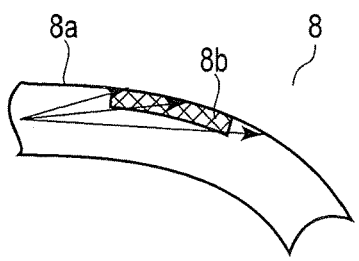
FIG. 3C is an illustration of a light transmission amount used when the optical fiber sensor is bent toward the opposite side of the shape detector.

In the insertion section 7, the elongated shape sensor 8 is provided to detect the entire shape of the insertion section 7. The shape sensor 8 is, for example, an optical fiber sensor (which will be described as an optical fiber sensor 8 hereinafter). In the optical fiber sensor 8, a plurality of detection points are so provided that they can detect the entire shape of the insertion section 7. The detection points are arranged and distributed in the longitudinal direction of the optical fiber sensor 8 over almost the entire length of the optical fiber sensor 8. The detection points are light absorbers (hereinafter referred to as shape detectors) 8*b* provided on one side of an optical fiber 8*a* that forms the optical fiber sensor 8, as shown in FIG. 3A to FIG. 3C, for example. The shape detectors 8*b* absorb light the intensity of which corresponding to the bending angle of the optical fiber 8*a*.

Therefore, the optical fiber sensor 8 utilizes a phenomenon in which the intensity of light absorbed by each of the shape detectors 8*b* increases or decreases depending on the bending angle of the optical fiber 8*a*. In the optical fiber sensor 8, therefore, the intensity of light transmitted through the optical fiber 8*a* decreases if the light absorbed by the shape detectors 8*b* increases as the bending angle of the optical fiber 8*a* becomes larger. Accordingly, the optical fiber sensor 8 emits an optical signal with light intensity corresponding to the bending angle of the optical fiber 8*a*.

The optical fiber sensor 8 includes, e.g. the optical fiber 8*a* as described above. If, therefore, the insertion section 7 is bent and accordingly the optical fiber 8*a* is bent, part of light transmitting through the optical fiber 8*a* is absorbed by the light absorbers of the shape detectors 8*b*. The shape detectors 8*b* are configured by removing part of a clad of the optical fiber 8*a* and then coating the removed part with a light-absorbing member or a coloring agent. In other words, the shape detectors 8*b* are provided on one side of the optical fiber 8*a* to absorb part of the light transmitted in accordance with the bending of the optical fiber 8*a*. That is, the shape detectors 8*b* change the optical characteristics of the optical fiber 8*a*, e.g. the light transmission amount thereof.

FIG. 3A shows a light transmission amount used when the optical fiber 8*a* is bent toward the shape detector 8*b*, FIG. 3B shows a light transmission amount used when the optical fiber 8*a* is not bent, and FIG. 3C shows a light transmission amount used when the optical fiber 8*a* is bent toward the opposite side of the shape detector 8*b*. As shown in these figures, the light transmission amount is the largest when the optical fiber 8*a* is bent toward the shape detector 8*b*, and it becomes smaller when the optical fiber 8*a* is not bent and much smaller when the optical fiber 8*a* is bent toward the opposite side of the shape detector 8*b*.

The optical fiber sensor 8 becomes a bending sensor by providing one shape detector 8*b*. The optical fiber sensor 8 can detect the entire three-dimensional shape of the insertion section 7 by providing a plurality of shape detectors 8*b* in the longitudinal direction and the circumferential direction of the insertion section 7.

The optical fiber sensor 8 may include, e.g. an optical means for attaching a different color agent to the shape detectors 8*b* and separating light in its wavelength. In the optical fiber sensor 8, therefore, a plurality of shape detectors 8*b* can be provided in a single optical fiber.

If a plurality of optical fibers including the shape detectors 8*b* are bound, a bend angle can be detected at a plurality of points. If the number of shape detectors 8*b* per optical fiber is increased, the number of optical fibers 8*a* can be decreased.

If a plurality of optical fibers 8*a* are bound, it is possible to enhance independence in detecting a bending angle of each optical fiber 8a by the shape detectors 8b of the optical fiber 8a. Accordingly, it is possible to improve detection accuracy for each of the shape detectors 8b and thus improve noise resistance.

In the insertion section 7, a plurality of shape detectors 8b is provided at given intervals, e.g. 10-cm intervals. If a plurality of shape detectors 8b are provided at these intervals, the overall bending shape of the insertion section 7 can be detected with high accuracy. If the interval between shape detectors 8b becomes longer than 10 cm, for example, the number of shape detectors 8b can be decreased to achieve cost reduction and simplify the system configuration for detecting the bending shape.

Incidentally, the insertion section 7 can be bent in an arbitrary direction by, e.g. an operator. To detect the bending shape of the insertion section 7 in three dimensions, a plurality of (usually two) detectors 8b have only to be provided in different circumferential directions in substantially the same location in the longitudinal direction of the insertion section 7. The detectors 8b can thus detect bending amounts in different two directions. If the different directions are combined, bending amounts in all directions can be obtained, with the result that the bending shape of the insertion section 7 can be detected in three dimensions.

The distal end of the optical fiber sensor 8 includes a reflection portion that reflects the received light toward the proximal end thereof.

Figure 4:
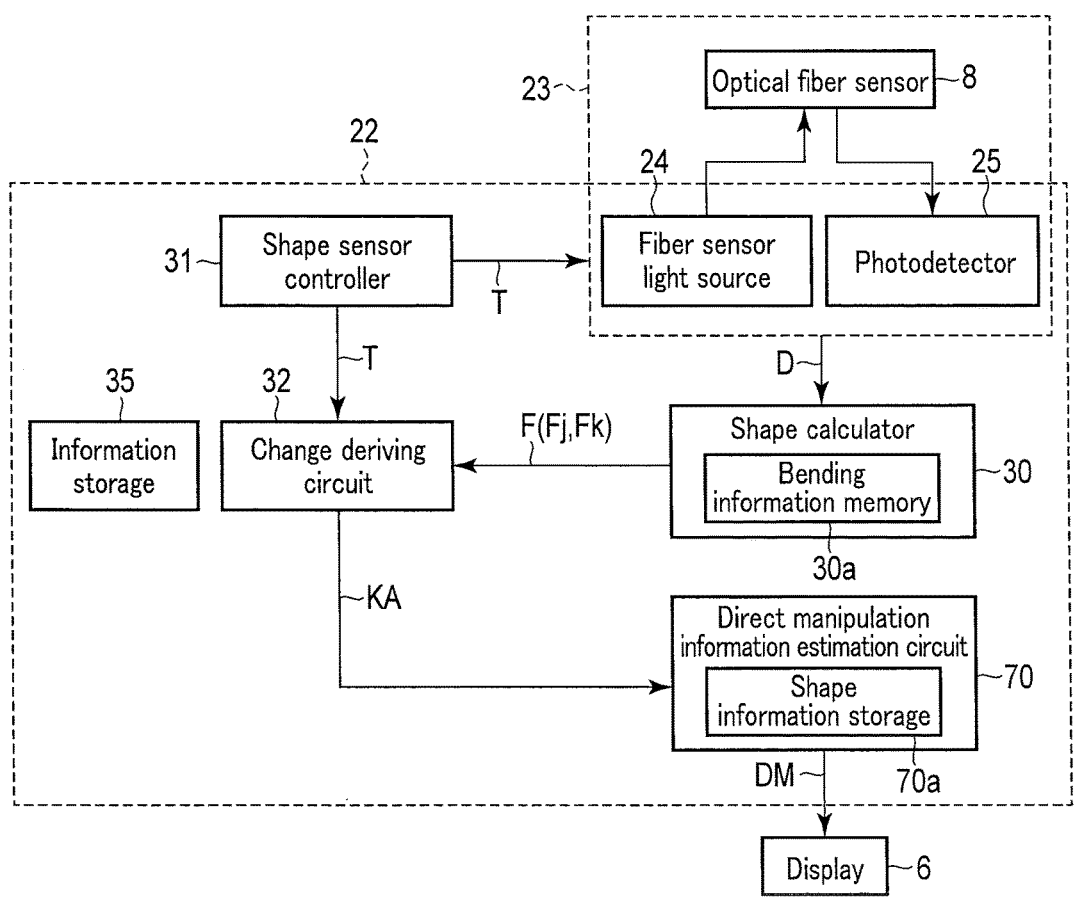
FIG. 4 is a block diagram showing a support information circuit of the endoscope system to which the insertion/removal apparatus of the present invention is applied.

As shown in FIG. 4, a shape sensor unit 23 detects a change in intensity of light guided to the optical fiber sensor 8 and includes a fiber sensor light source 24 and a photodetector 25. The optical fiber sensor 8 is provided in the insertion section 7. The fiber sensor light source 24 and the photodetector 25 are provided in the support information circuit 22.

The fiber sensor light source 24 emits detection light. The detection light emitted from the fiber sensor light source 24 is incident on the optical fiber sensor 8, guided by the optical fiber sensor 8 and then incident on the photodetector 25. At this time, the detection light passes through the shape detectors 8b provided in the optical fiber sensor 8. The light that has passed through the shape detectors 8b is reflected by the reflection portion provided at the distal end of the optical fiber sensor 8. The reflected light passes through the shape detectors 8b again and then enters the photodetector 25. The photodetector 25 detects the incident light, and a signal processing circuit (not shown) converts the light intensity of the detected light into a detection signal D and outputs the detection signal D. The detection signal D is transmitted to a calculation section of insertion section shape upon detection (referred to as a shape calculator) 30.

The insertion section 7 and the control section 9 are mechanically connected to each other. The control section 9 and the cable 10 are also mechanically connected to each other.

[Endoscope Main Body]

The endoscope main body 4 includes the light source section 20, the video processor 21, the support information circuit 22 and a main body memory 40, as shown in FIG. 1. The light source section 20 includes lamps such as a xenon lamp and a halogen lamp or semiconductor light sources such as an LED and a laser. Furthermore, a light guide is provided to be inserted through the cable 10, the control section 9 and the insertion section 7. Accordingly, when the light source section 20 emits light, the light is emitted as illumination light from the illumination section 13 provided at the distal-end portion 7a of the insertion section 7, through the light guide or the like. The illumination light enters the observation target object 2 to illuminate the internal space 3 of the observation target object 2.

The video processor 21 processes an imaging signal output from the image sensor 7d mounted at the distal-end portion 7a of the insertion section 7 to acquire an observation image of the inner surface in the internal space 3 of the observation target object 2. The imaging signal output from the image sensor 7d is transmitted to the video processor 21 through the insertion section 7, the control section 9, and a signal line provided inside the cable 10. The video processor 21 converts the acquired observation image into an observation image signal that can be displayed on the display 6, and transmits the observation image signal to the display 6.

FIG. 4 is a block diagram of the support information circuit 22. The support information circuit 22 includes part of the shape sensor unit 23. The shape sensor unit 23 includes the optical fiber sensor 8, the fiber sensor light source 24 and the photodetector 25. Incidentally, the fiber sensor light source 24 and photodetector 25 are included in the support information circuit 22, and the optical fiber sensor 8 is not included in the support information circuit 22. The shape sensor unit 23 outputs a detection signal D indicating light intensity corresponding to the bending shape of the insertion section 7. The configuration and operation of the shape sensor unit 23 will be described in detail later.

The support information circuit 22 functions as an operation support section for supporting the insertion and removal of the insertion section 7 into/from the observation target object 2. Upon receiving the detection signal D from the shape sensor unit 23, the support information circuit 22 processes the detection signal D and outputs support information for supporting operator's operation and manipulation, i.e. the direct manipulation information DM which is at least one of the insertion/removal amount and the rotation amount of the insertion section 7. The support information circuit 22 includes the shape calculator 30, a shape sensor controller 31, an insertion section shape time change deriving circuit (referred to as a change deriving circuit hereinafter) 32, an information storage 35, and a direct manipulation information estimation circuit 70.

Incidentally, the fiber sensor light source 24 and the photodetector 25 which are part of the shape sensor unit 23 are included in the support information circuit 22. The shape sensor unit 23 includes a signal processing circuit (not shown) for processing the output signal of the photodetector 25 and outputting the detection signal D.

[Operation at Turned On]

If the system 1 is turned on by an operator, the shape sensor unit 23 and the support information circuit 22 are also turned on. Accordingly, the shape sensor unit 23 can detect a bending shape of the insertion section 7. Thus, the shape sensor unit 23 sends to the shape sensor controller 31 a detectable signal (Ready signal) indicating that the shape of the insertion section 7 can be detected.

[Operation of Shape Sensor Controller 31]

If the shape sensor controller 31 receives a detectable signal to recognize that the shape sensor unit 23 is in a detectable state, it outputs first to n-th timing signals T. As for the first to n-th timing signals T, the first high-level signal is defined as a first timing signal, the next high-level signal is defined as a second timing signal, and the subsequent high-level signals are defined as the j-th, k-th, . . . n-th (n=a natural number) timing signals. The intervals at which the timing signals T are generated can be set as appropriate according to the contents of target support information, operator requests, operation speeds of the support information circuit 22 and the shape sensor unit 23, etc. The first to n-th timing signals T may be generated periodically at regular intervals, or the intervals between the first to n-th timing signals may be changed according to circumstances.

[Operation of Shape Sensor Unit 23]

The shape sensor unit 23 receives the first to n-th timing signals T from the shape sensor controller 31, receives an optical signal from the shape detectors 8b in response to the first to n-th timing signals T, and outputs a detection signal D corresponding to the optical signal. Regarding the operation of the optical fiber sensor 8, its description will be omitted because a publicly known operation can be used.

Specifically, the shape sensor unit 23 turns on power to cause the fiber sensor light source 24 to light up. The fiber sensor light source 24 emits detection light continuously with basically the same brightness. The detection light is incident on the incident end of the optical fiber 8a of the optical fiber sensor 8. The optical fiber sensor 8 guides the detection light incident from the incident end of the optical fiber 8a and emits the detection light from the emission end of the optical fiber 8a through the shape detectors 8b provided in the optical fiber sensor 8. The light emitted from the emission end of the optical fiber 8a is incident on the light detector 25.

If the optical fiber sensor 8 is bent together with the bending of the insertion section 7, the intensity of light absorbed by the shape detectors 8b varies according to the bending angle of the insertion section 7. For example, the intensity of light absorbed by the shape detectors 8b includes as the bending angle of the optical fiber 8a becomes larger. Accordingly, the light transmitted through the optical fiber 8a decreases as the bending angle of the optical fiber 8a becomes larger. Thus, the optical fiber sensor 8 outputs an optical signal with light intensity corresponding to the bending angle of the insertion section 7. The optical signal output from the optical fiber sensor 8 is incident on the photodetector 25. The photodetector 25 receives the incident optical signal and converts it into an electrical signal, and the signal processing circuit outputs the electrical signal as a detection signal D corresponding to the light intensity of the optical signal.

The shape sensor unit 23 sets a flag to the detection signal D so as to associate the optical signals from the shape detectors 8b provided in the optical fiber sensor 8 with the first to n-th timing signals T and distinguish among the optical signals from the shape detectors 8b. The detection signal D is transmitted to the shape calculator 30.

[Operation of Shape Calculator 30]

The shape calculator 30 processes the detection signal D output from the shape sensor unit 23 and outputs the processed signal as information of insertion section shape upon detection (referred to as insertion section shape information hereinafter) which is shape information of the insertion section 7.

The shape calculator 30 includes a bending information memory 30a. The bending information memory 30a stores information indicating the relationship between the bending amount of the insertion section 7 and the variation of light intensity represented by the detection signal D output from the shape sensor unit 23. The bending information memory 30a also stores information about the number of detection points of the optical fiber sensor 8, the arrangement positions of the detection points and the bending directions (X direction and Y direction) to be detected by the detection points.

Therefore, the shape calculator 30 calculates the bending direction and magnitude of the insertion section 7 that is bent, based on the detection signal D output from the shape sensor unit 23 and the information stored in the information memory 30a and outputs a result of the calculation as the insertion section shape information F.

[Operation of Shape Sensor Controller 31]

The shape sensor controller 31 outputs a timing signal T to take timing with which the shape sensor unit 23 detects a bending shape of the insertion section 7. The timing signal T is a square wave that becomes a high level in a fixed period, for example. When j and k are different natural numbers smaller than n (n is a natural number of 2 or more), if j is smaller than k (j<k), the shape sensor controller 31 outputs timing signal T of square wave that become a high level with the first to n-th timings. The first to n-th timing signals T include a j-th timing signal T and a k-th timing signal T.

Figure 5:
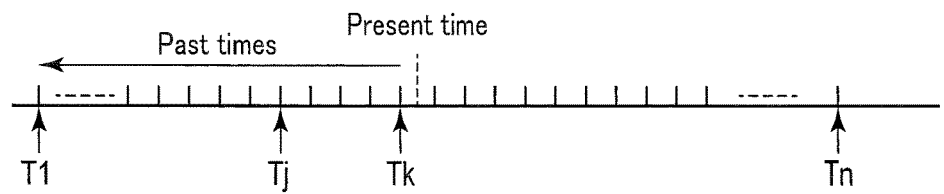
FIG. 5 is a chart showing an image of timing signal T output as time passes in the apparatus.

FIG. 5 shows timing signal Tn output from the shape sensor controller 31. When the timing signal T is output, for example, the j-th and k-th timing signals Tj and Tk have been output.

[Operation of Change Deriving Circuit 32]

The change deriving circuit 32 receives the timing signal T from the shape sensor controller 31. For example, the change deriving circuit 32 receives insertion section shape information F (referred to as the j-th insertion section shape information Fj hereinafter) from the shape calculator 30 when a j-th timing signal T is generated, and receives insertion section shape information F (referred to as the k-th insertion section shape information Fk hereinafter) from the shape calculator 30 when the k-th timing signal T is generated. For convenience's sake, the j-th insertion section shape information Fj represents the j-th insertion section shape upon detection. Similarly, for convenience's sake, the k-th insertion section shape information Fk represents the k-th insertion section shape upon detection.

The change deriving circuit 32 compares the j-th insertion section shape information Fj and the k-th insertion section shape information Fk which are received from the shape calculator 30, extracts a similar shape region and a dissimilar shape region in the j-th insertion section shape information Fj and the k-th insertion section shape information Fk. The change deriving circuit 32 outputs a result of the extraction to the direct manipulation information estimation circuit 70 as shape change information KA. The direct manipulation information estimation circuit 70 stores the shape change information KA in a shape information storage 70a.

Figure 6:
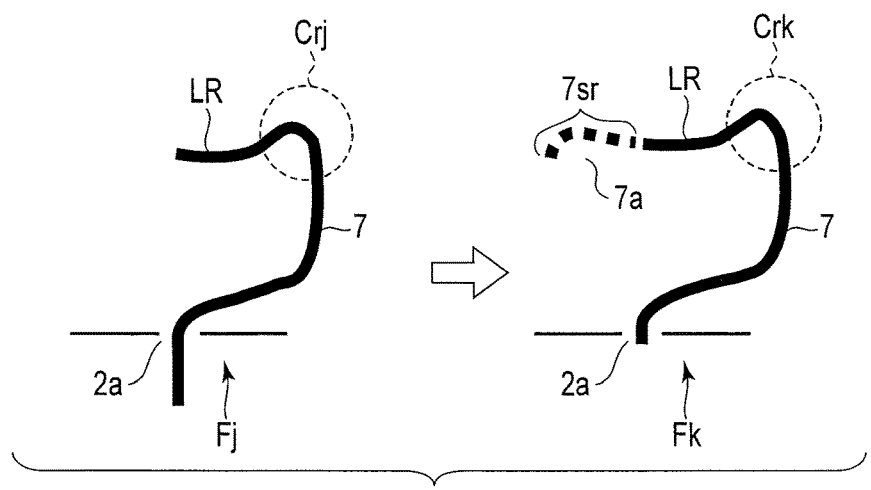
FIG. 6 is an illustration of the j-th and k-th insertion section shape information upon detection corresponding to the j-th and k-th timing signals in the apparatus.

FIG. 6 shows the j-th insertion section shape information Fj and the k-th insertion section shape information Fk. The j-th insertion section shape information Fj and k-th insertion section shape information Fk include similar shape regions LR whose shapes are similar to each other. A portion including the distal-end portion 7a of the insertion section 7 by the k-th insertion section shape information Fk includes an insertion section moving region 7sr. The insertion section moving region 7sr is a portion in which the insertion section 7 moves during the period from when the j-th timing signal Tj is generated until when the k-th timing signal Tk is generated.

In other words, upon receipt of an operator's manipulation, the insertion section 7 moves in the internal space 3 of the observation target object 2 by the insertion section moving region 7sr during the period from when the j-th timing signal Tj is generated until when the k-th timing signal Tk is generated. During this period, the shape of the similar shape region LR in the insertion section 7 does not change as shown in FIG. 15.

The reason why the shape of the similar shape region LR does not change is as follows. When an operator performs an insertion manipulation, the insertion section 7 moves into the internal space 3 of the observation target object 2 while its shape conforms to the inner surface of the internal space 3 of the observation target object 2. As the insertion section 7 moves, the shape of the insertion section 7 conforms to the inside of the internal space 3 of the observation target object 2 even during the period from when the j-th timing signal Tj is generated until when the k-th timing signal Tk is generated. Therefore, the shape of the insertion section 7 does not change in the similar shape region LR when the j-th timing signal T is generated or in the similar shape region LR when the k-th timing signal T is generated.

It is a point to be noted here that the position of the insertion section 7 corresponding to each position of the similar shape region LR is changed in the j-th insertion section shape information Fj and the k-th insertion section shape information Fk. In other words, the insertion section 7 is moved by its insertion in the j-th insertion section shape information Fj and the k-th insertion section shape information Fk; thus, the detection signals output from the shape detectors 8b at the detection points of the shape sensor 8 are different from one another, but there are similar shape regions LR whose shapes are substantially equal to each other in the j-th insertion section shape information Fj and k-th insertion section shape information Fk calculated by the shape calculator 30.

The change deriving circuit 32 compares the j-th insertion section shape information Fj and the k-th insertion section shape information Fk. As a result of the comparison, the change deriving circuit 32 extracts the similar shape regions LR whose shapes are substantially equal to each other and the regions other than the similar shape regions LR.

Figure 7:
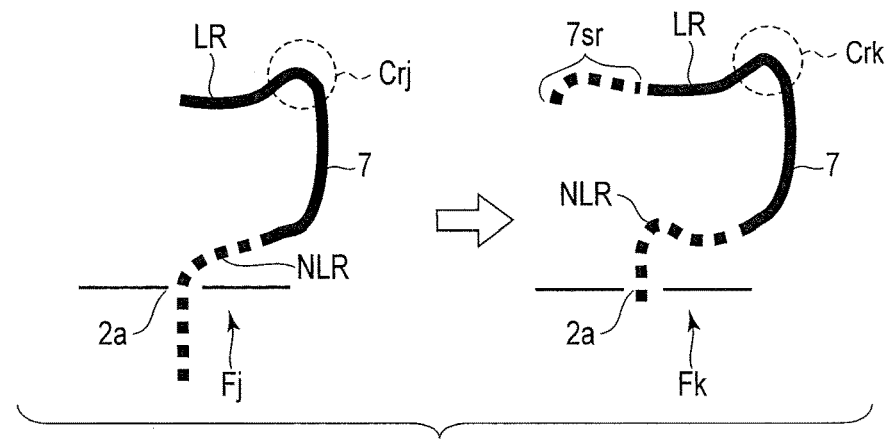
FIG. 7 is an illustration of three regions of an insertion section shape dissimilar region NLR, an insertion section moving region 7sr and an insertion section retreating region in the insertion section of the apparatus.

Each of the regions other than the similar shape regions LR includes three regions of an insertion section shape dissimilar region NLR, an insertion section moving region 7sr and an insertion section retreating region (not shown), for example, as shown in FIG. 7. The insertion section retreating region will be described later. FIG. 7 shows an example in which an operator's manipulation moves the distal-end portion of the insertion section 7 by the length of the insertion section moving region 7sr and further an insertion section similar shape region LR is generated close to the control section 9.

The insertion section shape dissimilar region NLR is a region that simply differs in shape clearly from the others. The insertion section moving region 7sr is, for example, a region which is not present when the j-th timing signal Tj is generated but newly appears when the k-th timing signal Tk is generated.

The insertion section retreating region is, for example, a region which is present when the j-th timing signal Tj is generated and disappears when the k-th timing signal Tk is generated. In other words, contrary to the insertion section moving region 7sr, the insertion section retreating region is, for example, a state such that a portion of the insertion section shape similar region LR is lost by a retreat of the insertion section 7.

When the insertion section 7 is shaped as shown in FIG. 7, the change deriving circuit 32 extracts insertion section similar shape regions LR whose shapes are substantially equal to each other, insertion section dissimilar shape regions NLR whose shapes are different from each other, and an insertion section moving region 7sr appearing when the k-th timing signal Tk is generated, and outputs a result of the extraction to the direct manipulation information estimation circuit 70 as shape change information KA.

[Operation of Direct Manipulation Information Estimation Circuit 70]

The direct manipulation information estimation circuit 70 estimates at least one of the insertion/removal manipulation and the rotation manipulation, which are performed by an operator, and outputs the estimated one as direct manipulation information DM. Assuming that the shape change of the insertion section 7 is a result of the operator's manipulation, the direct manipulation information estimation circuit 70 estimates a manipulation, which is performed during a period from the generation of the j-th timing signal Tj to that of the k-th timing signal Tk, on the basis of the shape change information KA derived by the change deriving circuit 32, and outputs the estimated manipulation as direct manipulation information DM.

Almost all of the j-th insertion section shape Fj become the insertion section similar shape region LR in the internal space 3 which is inside the insertion opening 2a of the observation target object 2 as shown in FIG. 6. In the k-th insertion section shape Fk, an operator's manipulation moves the insertion section 7 into the internal space 3 of the observation target object 2 by the length of the insertion section moving region 7sr.

Therefore, the direct manipulation information estimation circuit 70 estimates that the operator performs a push operation in the insertion direction to move the insertion section 7 into the internal space 3 of the observation target object 2 by the length of the insertion section moving region 7sr.

The direct manipulation information estimation circuit 70 estimates that the type of the manipulation is a push and the direction of the manipulation is the central axis direction of the insertion section 7 exposed from the insertion opening 2a. The insertion amount of the insertion section 7 is the length of the insertion section moving region 7sr.

The shape sensor unit 23 used in this embodiment can detect a bending direction of the insertion section 7. It is thus possible to determine the bending directions of, e.g. X and Y directions as one of the manipulation states of the insertion section 7 from detection signals D output from the shape sensor unit 23 when the j-th and k-th timing signals Tj and Tk are generated, even if each insertion section similar shape region LR has the same shape. For example, if it is determined that there is no change in the X and Y directions from the detection signals D output from the shape sensor unit 23, the direct manipulation information estimation circuit 70 estimates that the insertion section 7 is simply inserted. If there is a change in the X and Y directions from the detection signals D to the contrary, the direct manipulation information estimation circuit 70 estimates that the insertion section 7 is rotated.

There is a case where an insertion section moving region 7sr, an insertion section retreating region or an insertion section shape dissimilar region NLR as shown in FIG. 6 is not present in the insertion section close to the distal end of the insertion section similar shape region RL. This case indicates that the distal end of the insertion section 7 is stopped.

There is a case where an insertion section dissimilar shape region NLR is present in the insertion section 7 closer to the control section 9 than the insertion section similar shape region LR. In this case, it is understood that the insertion section shape dissimilar region NLR is caused by operator's manipulation, i.e. operator's insertion. The direct manipulation information estimation circuit 70 estimates an insertion/removal amount required to change the j-th insertion section shape dissimilar region NLR to the k-th insertion section shape dissimilar region NLR.

When an operator's manipulation moves the distal-end portion of the insertion section 7 by the length of the insertion section moving region 7*sr* as shown in FIG. 7 and further an insertion section shape similar region LR is generated close to the control section 9, the direction of the operator's manipulation corresponds to the insertion direction of the insertion section 7. The amount of manipulation is substantially equal to the sum of the length of the insertion section moving region 7*sr* and the length corresponding to the insertion amount required to cause the insertion section dissimilar shape region NLR.

The length of the insertion section moving region 7*sr* can be estimated from the locations of the shape detectors 8*b*, which are provided on a sensor to sense shape characteristic portions Crj and Crk of the insertion section 7 as shown in, e.g. FIG. 6, or the optical fiber sensor 8 of the shape sensor unit 23, on the insertion section 7. The characteristic portions Crj and Crk are located in a bent portion of the insertion section 7. If, however, they are located in the same position on the j-th and k-th insertion section similar shape regions LR, they can be located in another position, such as the distal end of the insertion section similar shape region LR. The characteristic portion Crj is a shape portion that appears when the j-th timing signal T is generated, and the characteristic portion Crk is a shape portion that appears when the k-th timing signal T is generated.

If a shape detector 8*b* that is located, e.g. 20 cm from the distal-end portion 7*a* of the insertion section 7 is exactly aligned with the top of the characteristic portion Crj when the j-th timing signal Tj is generated, it is understood that the characteristic portion Crj is located 20 cm from the distal end of the insertion section 7.

If, at the intermediate location between another shape detector 8*b* that is located, e.g. 30 cm from the distal-end portion 7*a* of the insertion section 7 and another shape detector 8*b* that is located, e.g. 40 cm from the distal-end portion 7*a*, further shape detector 8*b* is located and the further shape detector 8*b* is exactly aligned with the top of the characteristic portion Crk when the k-th insertion section shape Fk is generated, it is understood that the characteristic portion Crk is located 35 cm from the distal end of the insertion section 7.

Thus, the amount of insertion/removal of the insertion section 7 into the internal space 3 of the observation target object 2, namely the length of the insertion section moving region GR is a difference between the position (35 cm) of the characteristic portion Crj at the time of generation of the j-th timing signal Tj and the position (20 cm) of the characteristic portion Crk at the time of generation of the k-th timing signal Tk: 35 cm−20 cm=15 cm.

As shown in FIG. 7, when the insertion section 7 includes the dissimilar shaped region NLR, the insertion/removal amount of the insertion section 7 needs to add a difference in the length of the dissimilar shaped region NLR in the insertion section 7. In this case, since the dissimilar shape region NLR is in the insertion section 7 close to the control section 9 than the insertion section similar shape region LR, the length of the insertion section moving region GR cannot be calculated using the positions of the characteristic portions Crj and Crk.

In the above case, the direct manipulation information estimation circuit 70 estimates an insertion/removal amount required to change the j-th insertion section shape dissimilar region NLR to the k-th insertion section shape dissimilar region NLR. If the insertion/removal amount required to change the j-th insertion section shape dissimilar region NLR to the k-th insertion section shape dissimilar region NLR is, for example, 5 cm, the direct manipulation information estimation circuit 70 calculates the insertion/removal amount of the insertion section 7 as 20 cm that is the length obtained by adding 5 cm to 15 cm that has previously been obtained.

Though the j-th insertion section shape information Fj and the k-th insertion section shape information Fk can be compared in the change deriving circuit 32, the direct manipulation information estimation circuit 70 may include the function of the change deriving circuit 32. More specifically, the direct manipulation information estimation circuit 70 may read, e.g. the j-th insertion section shape information Fj and the k-th insertion section shape information Fk stored in the shape information storage 70*a*, and compare the j-th insertion section shape information Fj and the k-th insertion section shape information Fk to estimate direct manipulation information DM including at least one of the insertion/removal amount and the rotation amount of the insertion section 7.

In the first embodiment, the j-th insertion section shape information Fj and the k-th insertion section shape information Fk is compared in the change deriving circuit 32. If, however, the direct manipulation information estimation circuit 70 includes the function of the change deriving circuit 32, the change deriving circuit 32 becomes unnecessary. The outputs of the shape sensor controller 31 and the shape calculator 30 are input to the direct manipulation information estimation circuit 70.

[Stored Information of Information Storage 35]

The information storage 35 stores the detection signal D output from the shape sensor unit 23 and various items of information transmitted in the support information circuit 22, such as the insertion section shape information F and shape change information KA, in association with the timing signal T.

The information storage 35 stores information of correspondence between a plurality of detection points provided in the optical fiber sensor 8, namely position information items of the light absorbers 8*a* and the detection signal D indicating light intensity corresponding to the bending angle of the insertion section 7 and the bending angle of the optical fiber disposed in the optical fiber sensor 8.

The information storage 35 can exchange information with the shape calculator 30, the shape sensor controller 31, the change deriving circuit 32 and the direct manipulation information estimation circuit 70 in the support information circuit 22 through a channel not shown. The information stored in the information storage 35 can properly be read out by the operator.

The information storage 35, main body memory 40 and bending information memory 30*a* may use storage areas of the same memory device in correspondence with one another. Common information can be stored in one of the main body memory 40, bending information memory 30*a* and information storage 35 and can be read out of it through a channel not shown.

An operation of the apparatus configured as described above will be described below.

When the shape sensor controller 31 receives a detectable signal to recognize that the shape sensor unit 23 is in a detectable state, it outputs first to n-th timing signals T.

The shape sensor unit 23 receives the first to n-th timing signals T from the shape sensor controller 31 and an optical signal whose light intensity corresponds to the bending angle of the insertion section 7 from the shape detectors 8*b* in response to the first to n-th timing signals T, and outputs a detection signal D corresponding to the optical signal.

Like in the above, the shape calculator 30 receives a detection signal D from the shape sensor unit 23, calculates the bending direction and magnitude of the insertion section 7 that is bent, based on the detection signal D (light intensity), and outputs a result of the calculation as the insertion section shape information F, such as the j-th insertion section shape information Fj and the k-th insertion section shape information Fk.

The change deriving circuit 32 compares the insertion section shape information Fj and the insertion section shape information Fk, extracts insertion section similar shape regions LR whose shapes are substantially equal to each other, insertion section dissimilar shape regions NLR whose shapes are different from each other, and an insertion section moving region 7sr appearing when the k-th timing signal Tk is generated or an insertion section retreating region, and outputs a result of the extraction as shape change information KA.

The direct manipulation information estimation circuit 70 calculates direct manipulation information DM that is at least one of the insertion/removal amount and the rotation amount on the basis of the shape change information KA output from the change deriving circuit 32.

As described above, according to the first embodiment, the insertion/removal amount or the rotation amount of the insertion section 7 can be detected since direct manipulation information DM including at least one of the insertion/removal amount and the rotation amount of the insertion section 7 is estimated based upon the insertion section shape information F output from the shape calculator 30, such as the j-th insertion section shape information Fj and the k-th insertion section shape information Fk which are acquired at different detection timings. For example, when an operator finds a lesion with an endoscope, he or she can see the lesion according to how much the insertion section 7 is inserted and rotated with reference to a known portion of the observation target object 3 of, e.g. a patient which the operator can identify by an image picked up by the endoscope, such as a portion which the insertion section 7 of the endoscope reaches after it passes through a sigmoid and a splenic flexure. The operator can thus find a lesion easily even though he or she tries to observe and treat the lesion again.

The support information circuit 22 may have a calibration function of determining a reference of the insertion/removal amount and the rotation amount at a given point of time, namely making the insertion/removal amount and the rotation amount zero, though it is not shown. When the operator looks at an image displayed on the display 6 of the endoscope and determines that the insertion section 7 reaches a place where the position of the insertion section 7 can be specified, such as a place which the insertion section 7 reaches after it passes through a sigmoid and a splenic flexure, the operator enables the calibration function.

To enable the calibration function, for example, a switch for calibration is turned on to return the insertion/removal amount and the rotation amount to zero. The support information circuit 22 can thus detect the insertion/removal amount and the rotation amount in a place where the operator can specify the position, namely a known place of the internal space 3 of the observation target object 2.

[Modification]

Another method of calculating direct manipulation information DM by the direct manipulation information estimation circuit 70, including the operation of the change deriving circuit 32, will be described with reference to FIG. 8.

Figure 8:
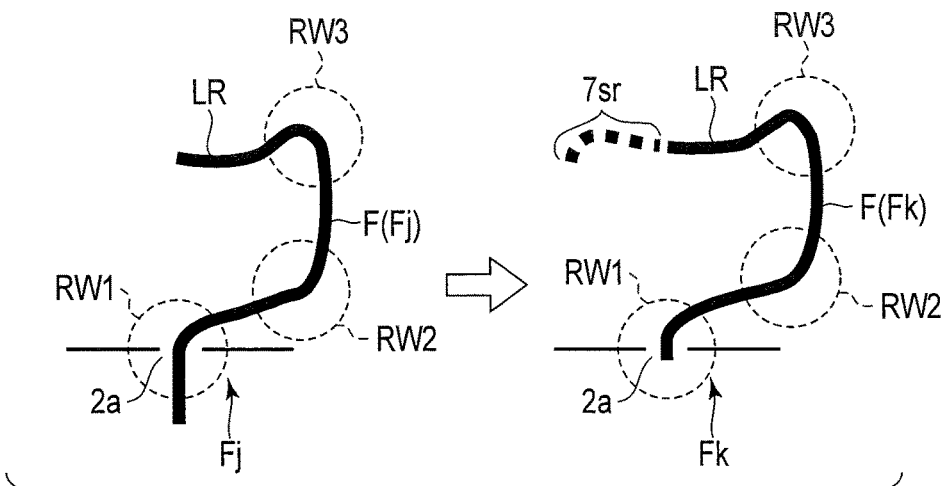
FIG. 8 is an illustration of a first inter-top distance same region to estimate direct manipulation information based on insertion section shape information by a direct manipulation information estimation circuit in the apparatus.

FIG. 8 shows that each of the j-th insertion section shape information Fj and the k-th insertion section shape information Fk includes three bending portions and the distances between the tops of the bending portions are substantially equal to each other. In other words, the spacings calculated from the coordinates of three tops in the insertion section shape information F (Fj, Fk) are substantially equal to each other, as are the directions calculated therefrom.

First, the change deriving circuit 32 calculates the coordinates of the tops of the bending portions of the insertion section shape as characteristic portions. The extracted three characteristic portions are referred to as first inter-top distance same regions RW1, RW2 and RW3. These can easily be obtained from the insertion section shape information F (Fj, Fk).

Then, the change deriving circuit 32 calculates a distance between the coordinates of the tops and a relative direction. In other words, in the j-th insertion section shape information Fj, the change deriving circuit 32 calculates a relative positional relationship and a spacing between the first inter-top distance same regions RW1, RW2 and RW3.

Similarly, in the k-th insertion section shape information F, the change deriving circuit 32 calculates a relative positional relationship and a spacing between the first inter-top distance same regions RW1, RW2 and RW3. Information of the relative positional relationship and the spacing is supplied to the direct manipulation information estimation circuit 70.

As the information of the relative positional relationship and the spacing, information of the coordinates can be arranged on a common coordinate axis or calculated as information of scalar quantity as a spacing and information of direction as a vector. Any technique and method can be employed if the relative positional relationships among the characteristic points can be compared.

Then, the direct manipulation information estimation circuit 70 compares the foregoing relative positional relationships and the spacings to extract characteristic portions (RW1, RW2, RW3) of the same positional relationship and spacing. It is very likely that the insertion section 7 of the endoscope, which must be as linear as possible if there is nothing therearound, will be bent by the internal structure of the observation target object 2. It is also very likely that the tops of the bending portions will be in contact with the observation target object 2. Furthermore, in the observation target object 2, too, a portion that is bent and brought into easy contact with the insertion section 7 is determined to some extent by the characteristics of the tube hole-like shape of the observation target object 2. For this reason, when the relative positional relationships and spacings between the tops of the bending portions are substantially equal, the insertion section 7 is very likely to be in contact with the same inner wall surface of the observation target object 2 and, in other words, it can be estimated that the insertion section 7 exists in the same location.

Since the relative positional relationships between the first inter-top distance same regions RW1, RW2 and RW3 in the j-th and k-th insertion section shape information F are substantially equal to each other, the direct manipulation information estimation circuit 70 determines that the first inter-top distance same regions RW1, RW2 and RW3 in the j-th and k-th insertion section shape information F are present in the same position for the observation target object 2.

Furthermore, based on the above information, the direct manipulation information estimation circuit 70 obtains a moving direction and a moving amount of the insertion section 7. If the j-th insertion section shape information Fj and the k-th insertion section shape information Fk are compared regarding the moving direction, it is found that the insertion section 7 extends into the observation target object 2 by the length of the insertion section moving region 7sr. Therefore, the moving direction is "an insertion direction" and the moving amount corresponds to "a length obtained by adding a difference in length between the first inter-top distance same regions RW1 to RW3 to a length that is substantially equal to the length of the insertion section moving region 7sr. Note that the moving amount can be obtained in the same manner as described above.

Even though the insertion section similar shape region LR cannot be extracted because the j-th and k-th insertion section shape information Fj and Fk as a whole are different in shape, the first inter-top distance same regions RW1, RW2 and RW3 in the j-th and k-th insertion section shape information Fj and Fk are extracted by the foregoing method, with the result that it can be determined that they are present in the same position for the observation target object 2 and the insertion/removal amount and the rotation amount can be obtained.

In this embodiment, the endoscopic main body 4 includes three units of the light source section 20, video processor 21 and support information circuit 22. Without limiting to this, the endoscope main body 4 may include, for example, a printer. The endoscope main body 4 may also include medical equipment required for a variety of procedures and treatments and all the other devices connectable to the endoscope system 1.

The light source section 20, video processor 21 and support information circuit 22 function individually in the endoscope main body 4. Without limiting to this, the light source section 20, video processor 21 and support information circuit 22 may function as one processing unit in the endoscope main body 4. Some functions of the light source section 20 and video processor 21 can be incorporated in the support information circuit 22. Furthermore, the endoscope main body 4 can be formed integrally with a unit other than three units of the light source section 20, video processor 21 and support information circuit 22.

In the support information circuit 22, the functions of the shape calculator 30, shape sensor controller 31, change deriving circuit 32, future shape estimation section 33 and manipulation estimation section 34 can be integrated into one processing unit.

In the support information circuit 22, each of the functions of the shape calculator 30, shape sensor controller 31, change deriving circuit 32, future shape estimation section 33 and manipulation estimation section 34 can be configured as an independent unit.

The support information circuit 22 can be combined freely, such as combined with another unit, taking into consideration various situations such as user's convenience and design easiness, and costs.

[Second Embodiment]

A second embodiment of the present invention will be described with reference to FIG. 9 below. In the second embodiment, the sections common to those of the foregoing first embodiment will not be described, but only different sections will be described in detail.

Figure 9:
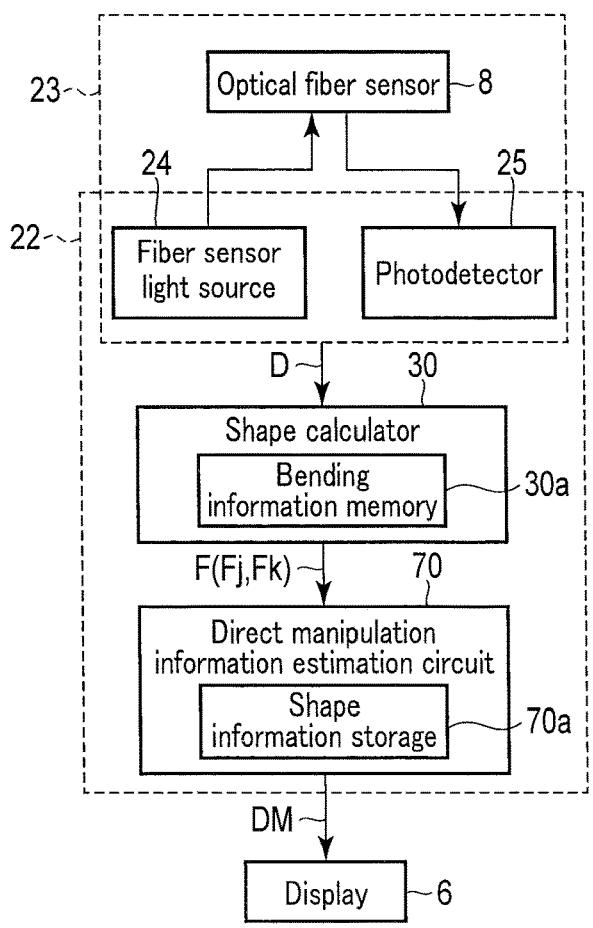
FIG. 9 is a block diagram showing a support information circuit according to a second embodiment of the endoscope system to which the insertion/removal apparatus of the present invention is applied.

FIG. 9 is a block diagram showing a support information circuit 22 according to the second embodiment of the endoscope system to which the insertion/removal apparatus of the present invention is applied. The support information circuit includes a direct manipulation information estimation circuit 70.

Figure 10A:
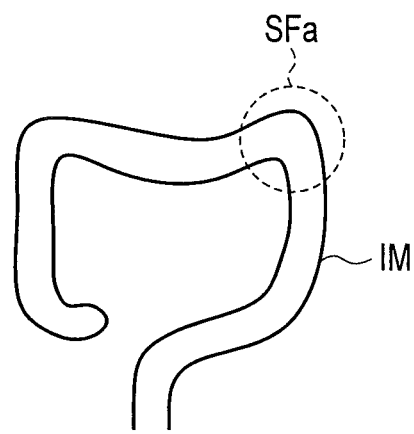
FIG. 10A is an illustration of target object inner shape information and a first inter-top distance same region to estimate direct manipulation information by the direct manipulation information estimation circuit in the apparatus.

The direct manipulation information estimation circuit 70 includes a shape information storage 70a in which target object inner shape information IM indicating a shape of the internal space 3 of the observation target object 2 is stored in advance. FIG. 10A is a schematic diagram showing an example of the target object inner shape information IM. The target object inner shape information IM indicates, for example, a shape of the human large intestine. The target object inner shape information IM is not limited to the shape of the human large intestine but may indicate a shape of an esophagus, a stomach, a blood vessel and the like.

The direct manipulation information estimation circuit 70 compares insertion section shape information F output from a shape calculator 30, e.g. the k-th insertion section shape information Fk and target object inner shape information IM stored in the shape information storage 70a to estimate direct manipulation information DM.

Figure 10B:
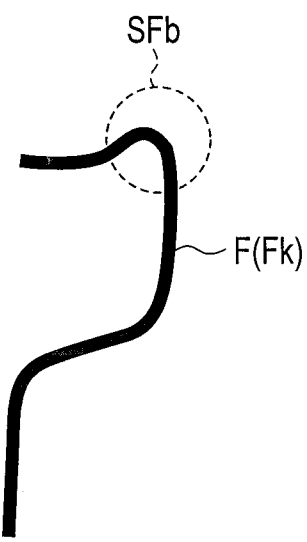
FIG. 10B is an illustration of a first inter-top distance same region in the insertion section shape information to estimate direct manipulation information by the direct manipulation information estimation circuit in the apparatus.

First, based on a result of the comparison of the insertion section shape information F including, e.g. the k-th insertion section shape information Fk and the target object inner shape information IM, the direct manipulation information estimation circuit 70 extracts a shape similar region on an insertion section 7 as an insertion section and target object similar shape region SF. FIG. 10B shows an insertion section and target object similar shape region SFb in the insertion section shape information F including, e.g. the k-th insertion section shape information Fk.

Next is a description of a method of estimating an insertion/removal amount of the insertion section.

Figure 11A:
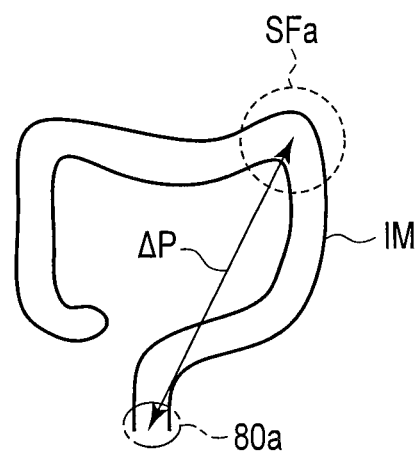
FIG. 11A shows an interval ΔP between a specific portion and an insertion section and target object similar shape region SFa in target object inner shape information IM estimated by the direct manipulation information estimation circuit in the apparatus.
Figure 11B:
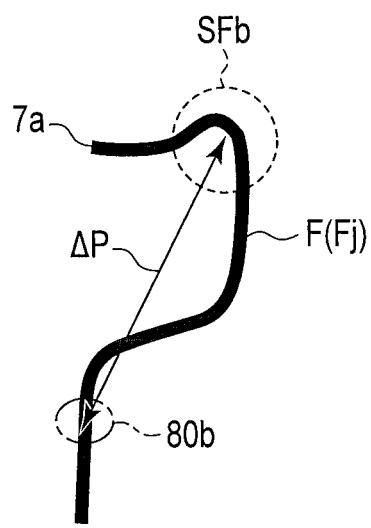
FIG. 11B shows an interval ΔP between a specific portion and an insertion section and target object similar shape region SFb in insertion section shape information F estimated by the direct manipulation information estimation circuit in the apparatus.

FIG. 11A shows a relative position $\Delta P$ of an entrance 80a that is a specific portion to an insertion section and target object similar shape region SFa on the target object inner shape information IM, and FIG. 11B shows a relative position $\Delta P$ of an entrance 80b that is a specific portion to an insertion section and target object similar shape region SFb on the insertion section shape information F. The target object inner shape information IM includes the entrance 80a that is a specific portion. The entrance 80a is stored in the shape information storage 70a as known information.

The direct manipulation information estimation circuit 70 calculates a relative position $\Delta P$ of the entrance 80a that is a specific portion to the insertion section and target object similar shape region SFa on the target object inner shape information IM, as shown in FIG. 11A.

The direct manipulation information estimation circuit 70 calculates a relative position $\Delta P$ to the insertion section and target object similar shape region SFb on the insertion section shape information F, namely, calculates a position of the entrance 80b that is a specific portion on the insertion section shape information F.

Then, the direct manipulation information estimation circuit 70 calculates a length from the position of the entrance 80b on the insertion section shape information F to the distal end of the insertion section shape information F, namely, calculates an insertion/removal amount of the insertion section 7 from the entrance 80b.

As described above, the direct manipulation information estimation circuit 70 can estimate a position of a specific portion on the insertion section shape information F, e.g. a position of the entrance 80b of the internal space 3 in the observation target object 2 on the basis of the target object inner shape information IM stored in the shape information storage 70a to calculate a length from the entrance 80b to the distal end portion 7a of the insertion section 7 and calculate an insertion/removal amount of the insertion section 7 that is inserted into the internal space 3 of the observation target object 2 from the length.

In the second embodiment, neither the shape sensor controller 31 nor the change deriving circuit 32 is essential because changes in shape of the insertion section 7, which are made as time passes, are not compared. Accordingly, the support information circuit 22 shown in FIG. 9 is configured to include neither the shape sensor controller 31 nor the change deriving circuit 32.

Next is a description of the operation of the apparatus configured as described above.

Like in the above, the shape calculator 30 calculates a bending direction and magnitude of the insertion section 7 that is bent, based on a detection signal D (light intensity) output from a shape sensor unit 23, and outputs the calculated bending direction and magnitude as insertion section shape information F, e.g. the k-th insertion section shape information Fk.

The direct manipulation information estimation circuit 70 compares the insertion section shape information F output from the shape calculator 30, e.g. the k-th insertion section shape information Fk and the target object inner shape information IM stored in the shape information storage 70a.

As a result of the comparison, the direct manipulation information estimation circuit 70 extracts insertion section and target object similar shape regions SFa and SFb, which are similar in shape of the insertion section 7 to the target object inner shape information IM, as shown in FIG. 10A and FIG. 10B.

The direct manipulation information estimation circuit 70 calculates a relative position ΔP of the entrance 80a that is a specific portion to the insertion section and target object similar shape region SFa on the target object inner shape information IM, as shown in FIG. 11A.

Then, the direct manipulation information estimation circuit 70 calculates a relative position ΔP to the insertion section and target object similar shape region SFb on the insertion section shape information F, namely a position of the entrance 80b that is a specific portion on the insertion section shape information F.

The direct manipulation information estimation circuit 70 estimates a length from the position of the entrance 80b on the insertion section shape information F to the distal end of the insertion section shape information F, namely an insertion/removal amount of the insertion section 7 from the entrance 80b. Note that a rotation amount can be obtained as in the first embodiment.

As described above, the second embodiment can bring about the same advantages as those of the first embodiment since the direct manipulation information DM is estimated by comparing the insertion section shape information F (e.g. k-th insertion section shape information Fk) output from the shape calculator 30 and the target object inner shape information IM stored in the shape information storage 70a.

In the foregoing first embodiment, relative direct manipulation information, namely a relative change in the insertion/removal amount and rotation amount of the insertion section 7 can be seen from a state at a certain point of time, but absolute direct manipulation information for the internal space 3 of the observation target object 2 cannot be seen. In the first embodiment, therefore, in order to detect direct manipulation information for the internal space 3 of the observation target object 2, for example, an operator needs to look at an image displayed on the display 6 of the endoscope apparatus and perform, e.g. an operation of depressing a calibration button in a place where the position of the insertion section 7 can be specified, such as a place which the insertion section 7 reaches after it passes through a sigmoid and a splenic flexure.

In contrast to the above, according to the foregoing second embodiment, direct manipulation information DM including at least one of the insertion/removable amount and the rotation amount of the insertion section 7 for the internal space 3 of the observation target object 2 can be estimated.

[Modification]

Another method of estimating the insertion/removal of the insertion section 7 will be described with reference to FIG. 12A and FIG. 12B.

FIG. 12B illustrates the insertion section shape information F including second inter-top distance same regions RW1b, RW2b and RW3b corresponding to three bending portions. FIG. 12A illustrates the target object inner shape information IM including the tops of bending portions (second inter-top distance same regions RW1a, RW2a and RW3a), the spacings between which are equal to each other and the directions of which are equal to each other.

First, the direct manipulation estimation section 70 calculates the coordinates of the tops of the bending portions as characteristic portions in the insertion section shape. The coordinates can easily be calculated from the insertion section shape information F.

Then, the direct manipulation estimation section 70 calculates a distance between the coordinates of the tops and a relative direction. In other words, the direct manipulation estimation section 70 calculates a relative positional relationship between the second inter-top distance same regions RW1b, RW2b and RW3b and a spacing between them.

Then, the direct manipulation estimation section 70 extracts the second inter-top distance same regions RW1a, RW2a and RW3a of the bending portions whose positional relationship is substantially equal to the relative positional relationship between the second inter-top distance same regions RW1b, RW2b and RW3b from the target object inner shape information IM.

As the information of the relative positional relationship and the spacing, information of the coordinates can be arranged on a common coordinate axis or calculated as information of scalar quantity as a spacing and information of direction as a vector. Any technique and method can be employed if the relative positional relationships among the characteristic points can be compared.

Since it can be estimated that the positional relationship between the second inter-top distance same regions RW1a, RW2a and RW3a and the positional relationship between the second inter-top distance same regions RW1b, RW2b and RW3b are the same, the direct manipulation estimation section 70 can estimate the positional relationship of the insertion section shape information F for the target object inner shape information IM. Based on this information, the direct manipulation estimation section 70 calculates the moving direction and the moving amount of the insertion section for the internal space 3 of the observation target object 2.

Even though the insertion section and target object similar shape region SFb cannot be extracted because the target object inner shape information IM and the insertion section shape information F as a whole are different in shape, the second inter-top distance same regions RW1a, RW2a and RW3a and RW1b, RW2b and RW3b in the target object inner shape information IM and the insertion section shape information F are extracted by the foregoing method, with the result that it can be determined that they are present in the same position for the observation target object, and the insertion/removal amount and the rotation amount for the internal space 3 of the observation target object 2 can be obtained.

Note that the present invention is not limited to the above embodiments.

In the foregoing embodiments, a fixed-shape generation attachment (abbreviated as attachment hereinafter) 90 can be provided as illustrated in FIG. 13. The position of the attachment 90 is fixed to the observation target object 2. The attachment 90 is shaped cylindrically, and the insertion section 7 is inserted into and removed from the cylindrical portion of the attachment 90. The attachment 90 includes a bending portion 91 that is bent to have a characteristic shape. With the bending portion 91 of the attachment 90, part of the insertion section 7 that passes through the attachment 90 is shaped to have a fixed bending shape.

Since the insertion section 7 passes through the attachment 90 when it is inserted into and removed from the observation target object 2, a bending portion is formed in a region of the insertion section 7 which corresponds to the attachment 90. Though the attachment 90 has corrugated shape and is shaped cylindrically to allow, e.g. the insertion section 7 to pass through the attachment 90, it may have another shape. Favorably, the attachment 90 has a characteristic shape such as bending to such a degree that the insertion section 7 is allowed to pass therethrough and, more favorably, it has a shape that the inside of the observation target object 2 cannot take.

The attachment 90 is not limited to the bending shape but can be shaped like a linear cylinder if it can be distinguished from the other portions. For example, the attachment 90 can be shaped like a linear cylinder with a length that the inside of the observation target object 2 cannot have. FIG. 14A to FIG. 14C each illustrate an example of another shape of the attachment 90. FIG. 14A illustrates an attachment 90 with a bending portion. FIG. 14B illustrates an attachment 90 that is bent with a preset small curvature. FIG. 14C illustrates an attachment 90 shaped like a linear cylinder with a length that the inside of an observation target object 2 cannot have.

It is favorable that the diameter of the cylindrical portion of the attachment 90 be slightly larger than that of the insertion section 7. Accordingly, the insertion section 7 is formed to conform to the shape of the attachment 90. If the insertion section 7 is caused to pass through the attachment 90, its part can be maintained to have a fixed shape such as bending.

Furthermore, the attachment 90 is fixed such that its position cannot be changed with respect to the observation target object 2. For example, it can be inserted into the entrance 80a of the internal space 3 in the observation target object 2 or fixed to the observation target object 2 with a tape or the like.

It can be considered that when the inner shape of the observation target object 2 greatly varies, it maybe difficult to extract a similar shape region LR and first inter-top distance same regions RW1, RW2 and RW3 as shown in FIG. 15. Even though the similar shape region LR and the first inter-top distance same regions RW1, RW2 and RW3 are difficult to extract, if the attachment 90 is used, its bending portion 91 allows the insertion section 7 to have a fixed shape in a fixed position with respect to the observation target object 2. Thus, the shape of, e.g. the bending portion 91 formed on the insertion section 7 by the attachment 90 is extracted as a similar shape region LR, and direct manipulation information DM can be estimated.

The attachment 90 is disposed outside the observation target object 2 in FIG. 13. However, it can be disposed inside the observation target object 2.

Figure 17:
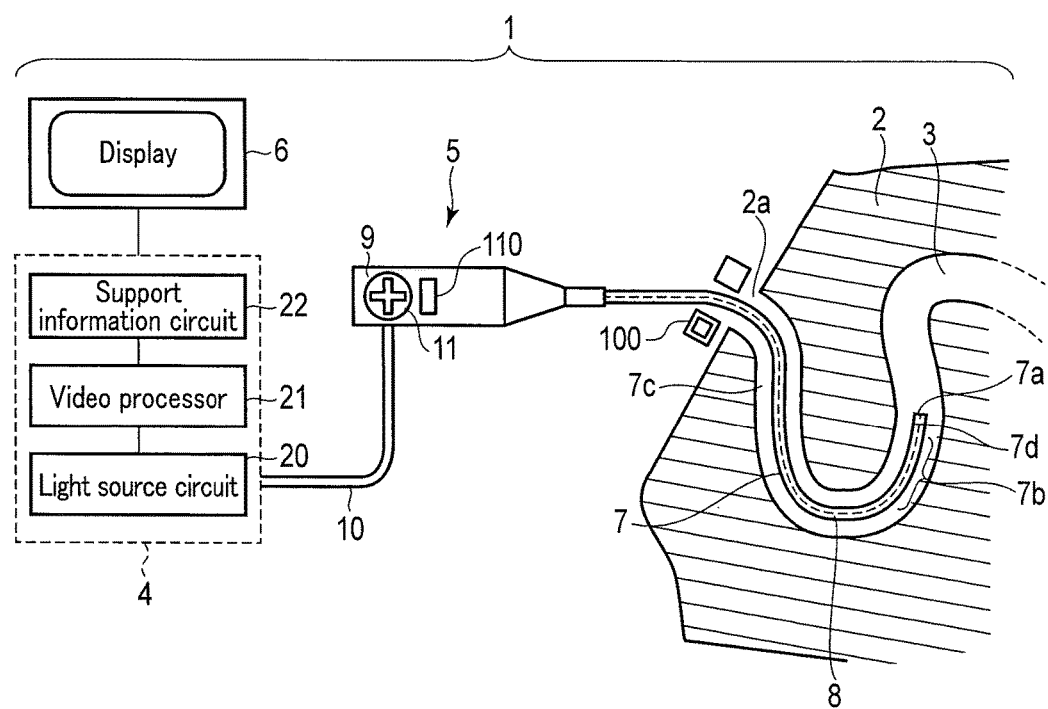
FIG. 17 is a configuration diagram showing an example of a modification to the present invention.

In the foregoing first and second embodiments, an insertion/removal rotation amount sensor 100 can be provided to directly sense information of at least one of the insertion/removal amount and the rotation amount of the insertion section 7 inserted into and removed from an observation target object 3 as shown in FIG. 16 and FIG. 17.

In the above case, the direct manipulation information estimation circuit 70 corrects the information sensed by the insertion/removal rotation amount sensor 100.

The insertion/removal rotation amount sensor 100 senses one or both of the insertion/removal amount and the rotation amount of the insertion section 7 using, e.g. an encoder and a speckle sensor. Since, however, the encoder and speckle sensor are likely to cause an error by skipping, the error is corrected using the direct manipulation information DM estimated by the direct manipulation information estimation circuit 70. Thus, the direct manipulation information estimation circuit 70 can estimate the direct manipulation information DM of the insertion/removal amount or the rotation amount with higher precision.

If the insertion/removal rotation amount sensor 100 is a sensor which cannot sense the absolute insertion/removal amount or rotation amount for the internal space 3 of the observation target object 2, an error is corrected using direct manipulation information DM of at least one of the insertion/removal amount and the rotation amount of the insertion section 7 inserted into and removed from the observation target object 3 estimated by the direct manipulation information estimation circuit 70 in the second embodiment, with the result that an insertion/removal amount and a rotation amount in the absolute position of the insertion section 7 inserted into the internal space 3 of the observation target object 2 can be estimated.

The shape sensor 8 is not limited to the optical fiber sensor.

As the shape sensor 8, any sensor can be used if it can detect the shape of the insertion section 7 inside the observation target object 2. For example, a plurality of magnetic coils can be arranged in the insertion section 7 and a magnetic antenna can be disposed outside the insertion section 7. In this case, the absolute position of the antenna can be confirmed and thus the insertion/removal rotation amount sensor 100 need not be used.

An X-ray camera can be used. In the case of medical endoscopes, a procedure for confirming a shape of the insertion section 7 in a living body and a relative position between the living body and the insertion section 7 by an X-ray camera has been known for a long time. In this case, the position and shape of an organ in the living body can be confirmed roughly and accordingly the inner profile of the observation target object 2 can be improved in precision and accuracy. In the case of X-ray cameras, if only one X-ray camera, only two-dimensional data is obtained. This case can be handled by processing the above-described configuration and operations two-dimensionally. As compared with three-dimensional information, the amount of information is reduced, but a fixed effect can be expected.

Furthermore, in all the embodiments described above, a sensor loaded onto the endoscope is directed to only the optical fiber sensor 8 as a shape sensor. For example, as shown in FIG. 17, an operation amount sensor 110 capable of directly sensing a manipulation amount of a manipulation handle 11 to detect a bending manipulation of the active bending portion 7b of the endoscope is disposed at the control section 9, and a manipulation amount that is the output of the operation amount sensor 110, namely a bending amount of the active bending portion 7b is used, with the result that part of the insertion section shape information F sensed by the shape sensor in all of the foregoing embodiments can be detected.

In the foregoing embodiments and their modifications, an endoscope is exemplified as a subject matter; however, the present invention is not limited to the endoscope. The present invention is favorable for all insertion/removal systems to perform a desired operation by inserting the flexible insertion section 7 into a tube hole. For example, treatment instruments and forceps to be inserted into the forceps channel of an endoscope for treatment, catheters to be inserted into blood vessels and lymphatic vessels for various treatments, various industrial observation/repair devices for maintenance of industrial piping, etc. are particularly favorable for the systems. Some of the insertion/removal systems may not have the function of performing an active manipulation and, in that case, the operator manipulation information L does not include "a bending manipulation" but the object can be attained by almost the same procedure, operation and function as described above.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An insertion/removal apparatus comprising:
   an insertion section with flexibility which is inserted into a target object to perform a desired operation;
   a shape sensor which detects bending of the insertion section with different detection timings and outputs a detection signal; and
   a controller comprising hardware, the controller being configured to:
      calculate insertion section shape information indicating a shape of the insertion section, based on the detection signal output from the shape sensor; and
      estimate direct manipulation information including at least one of an insertion/removal amount and a rotation amount of the insertion section inserted into and removed from the target object, based on the insertion section shape information,
   wherein the estimating comprises:
      comparing a plurality of items of insertion section shape information indicating shapes of the insertion section of the different detection timings stored in a memory,
      extracting regions whose shapes are similar on the insertion section as insertion section similar shape regions from a result of the comparison of the plurality of items of insertion section shape information, and
      estimating the direct manipulation information based on variations in position of the insertion section similar shape regions on the insertion section.

2. An insertion/removal apparatus comprising:
   an insertion section with flexibility which is inserted into a target object to perform a desired operation;
   a shape sensor which detects bending of the insertion section with different detection timings and outputs a detection signal;
   a controller comprising hardware, the controller being configured to:
      calculate insertion section shape information indicating a shape of the insertion section, based on the detection signal output from the shape sensor; and
      estimate direct manipulation information including at least one of an insertion/removal amount and a rotation amount of the insertion section inserted into and removed from the target object, based on the insertion section shape information,
   wherein the estimating comprises:
      comparing a plurality of items of insertion section shape information indicating shapes of the insertion section of the different detection timings stored in a memory,
      extracting a first inter-top distance same region in which intervals between tops of a plurality of bending portions of the insertion section are substantially equal to each other, and
      estimating the direct manipulation information based on variations in position of the first inter-top distance same region on the insertion section.

3. An insertion/removal apparatus comprising:
   an insertion section with flexibility which is inserted into a target object to perform a desired operation;
   a shape sensor which detects bending of the insertion section and outputs a detection signal; and
   a controller comprising hardware, the controller being configured to:
      calculate insertion section shape information indicating a shape of the insertion section, based on the detection signal output from the shape sensor; and
      estimate direct manipulation information including at least one of an insertion/removal amount and a rotation amount of the insertion section inserted into and removed from the target object, based on the insertion section shape information,
   wherein the estimating of the direct manipulation information is based on target object inner shape information that is an inner shape of the target object and the insertion section shape information.

4. The insertion/removal apparatus according to claim 3, wherein the estimating compares the insertion section shape information and the target object inner shape information, extracts insertion section and target object similar shape regions whose insertion section shapes are similar, and estimates the direct manipulation information based on a positional relationship between a position of the insertion section and target object similar shape region on the insertion section and a position of the target object corresponding to the insertion section and target object similar shape region.

5. The insertion/removal apparatus according to claim 3, wherein the estimating compares the insertion section shape information and the target object inner shape information, extracts a second inter-top distance same region in which intervals between tops of a plurality of bending portions of the insertion section are substantially equal to each other, and estimates the direct manipulation information based on a position of the second inter-top distance same region.

6. The insertion/removal apparatus according to claim 3, wherein the estimating estimates a position of a specific portion of the target object on the insertion section based on the insertion section shape information and the target object inner shape information.

7. The insertion/removal apparatus according to claim 6, wherein the estimating estimates the direct manipulation information from the position of the specific portion of the target object for the insertion section shape information.

8. The insertion/removal apparatus according to claim 1, further comprising a fixed-shape generation attachment whose position is fixed to the target object and which is formed to have a fixed shape by bending a region of the insertion section.

9. The insertion/removal apparatus according to claim 1, wherein the shape sensor includes a fiber sensor provided on the insertion section.

10. The insertion/removal apparatus according to claim 1, further comprising an insertion/removal rotation amount sensor which directly detects the direct manipulation information,
    wherein the fixed-shape generation attachment estimating corrects the direct manipulation information detected by the insertion/removal rotation amount sensor.

11. The insertion/removal apparatus according to claim 1, wherein the insertion section includes an endoscope insertion section to observe an inner surface of the target object.

12. An insertion section direct manipulation estimation method comprising:
    detecting bending of an insertion section with flexibility by a shape sensor when the insertion section is inserted into a target object to perform a desired operation;
    calculating insertion section shape information indicating a shape of the insertion section, based on the detection signal output from the shape sensor; and
    estimating direct manipulation information including at least one of an insertion/removal amount and a rotation amount of the insertion section inserted into and removed from the target object, based on the insertion section shape information,
    wherein the shape sensor detects bending of the insertion section with different detection timings, and
    wherein the estimating direct manipulation information includes:
        comparing a plurality of items of insertion section shape information which is stored in a shape information memory and which indicates shapes of the insertion section of the different detection timings;
        extracting regions whose shapes are similar on the insertion section as insertion section similar shape regions from a result of comparison of the plurality of items of insertion section shape information; and
        estimating the direct manipulation information based on variations in position of the insertion section similar shape regions on the insertion section.

13. A non-transitory storage medium, which non-transitory stores a computer-readable insertion section direct manipulation estimation program, causing a computer to achieve:
    an input function of inputting a detection signal output from a shape sensor to detect bending of an insertion section with flexibility inserted into a target object;
    an insertion section shape acquisition function of calculating insertion section shape information indicating a shape of the insertion section, based on the detection signal input by the input function; and
    a direct manipulation information estimation function of estimating direct manipulation information including at least one of an insertion/removal amount and a rotation amount of the insertion section inserted into and removed from the target object, based on the insertion section shape information,
    wherein the shape sensor detects bending of the insertion section with different detection timings, and
    wherein the direct manipulation information estimation function includes:
        a comparing function of computing a plurality of items of insertion section shape information which is stored in a shape information memory and which indicates shapes of the insertion section of the different detection timings;
        an extracting function of extracting regions whose shapes are similar on the insertion section as insertion section similar shape regions from a result of comparison of the plurality of items of insertion section shape information; and
        an estimating function of estimating the direct manipulation information based on variations in position of the insertion section similar shape regions on the insertion section.

* * * * *